US005613489A

United States Patent [19]

Miller et al.

[11] Patent Number: 5,613,489

[45] Date of Patent: Mar. 25, 1997

[54] PATIENT RESPIRATORY SYSTEM DRUG APPLICATOR

[75] Inventors: Warren C. Miller, Webster, Tex.; Robert J. McKinnon, Cheyenne, Wyo.

[73] Assignee: Westmed, Inc., Tucson, Ariz.

[21] Appl. No.: 351,660

[22] Filed: Dec. 7, 1994

[51] Int. Cl.$^6$ ..................... A61M 11/00

[52] U.S. Cl. ..................... 128/203.28; 128/200.14; 128/203.12

[58] Field of Search ..................... 128/205.13, 203.12, 128/203.28, 205.11, 205.24, 204.29, 200.14, 200.16

[56] References Cited

U.S. PATENT DOCUMENTS

| | | | |
|---|---|---|---|
| 3,906,996 | 9/1975 | DePass et al. | 128/205.11 |
| 3,967,619 | 7/1976 | Story et al. | 128/145.8 |
| 4,088,131 | 5/1978 | Elam et al. | 128/205.13 |
| 4,676,239 | 6/1987 | Humphrey | 128/203.28 |
| 4,823,784 | 4/1989 | Bordoni et al. | 128/200.14 |
| 5,020,530 | 6/1991 | Miller | 128/203.28 |
| 5,099,833 | 3/1992 | Michaels | 128/203.12 |

FOREIGN PATENT DOCUMENTS

| | | | |
|---|---|---|---|
| 293900 | 7/1928 | United Kingdom | 128/204.29 |

*Primary Examiner*—Aaron J. Lewis
*Assistant Examiner*—William J. Deane, Jr.
*Attorney, Agent, or Firm*—Sheridan Ross P.C.

[57] ABSTRACT

A respiratory system drug applicator for a patient is disclosed which may include a number of features to enhance the administration of the aerosolized drug to the patient. For instance, an adjustable flow regulator may be utilized which regulates the air flow during inhalation by the patient (during which the aerosolized drug is also administered to the patient's respiratory system), and thus affects the patient's breathing pattern. Moreover, a distensible drug reservoir which changes shape during inhalation and exhalation by the patient may be utilized. This may be used to provide biofeedback to the patient regarding the patient's breathing pattern.

14 Claims, 4 Drawing Sheets

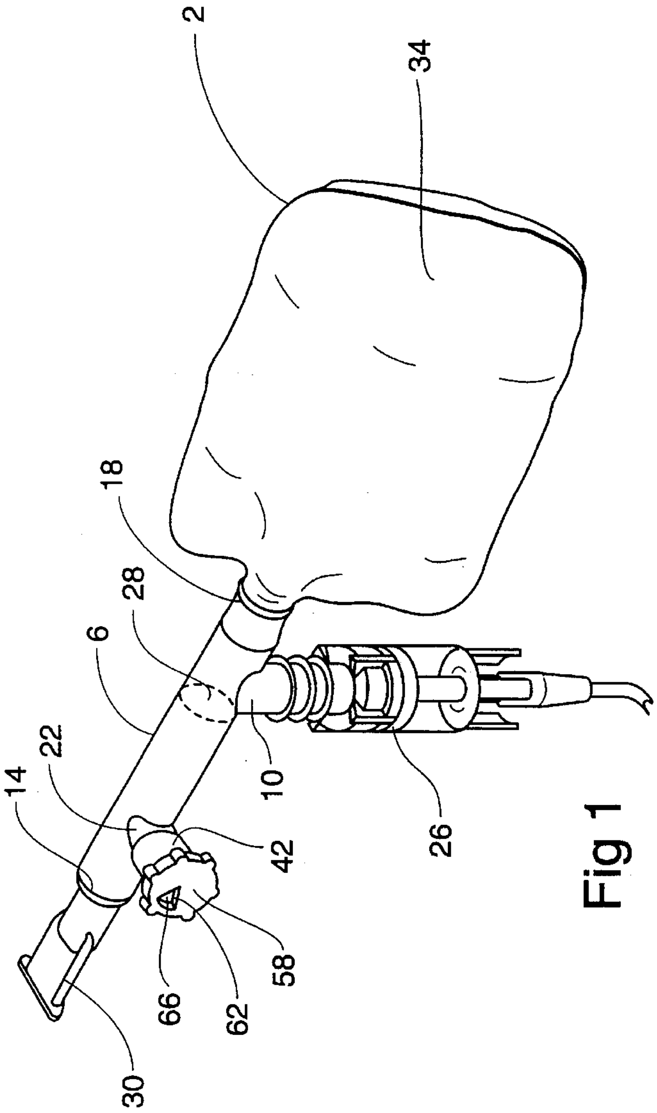
Fig 1
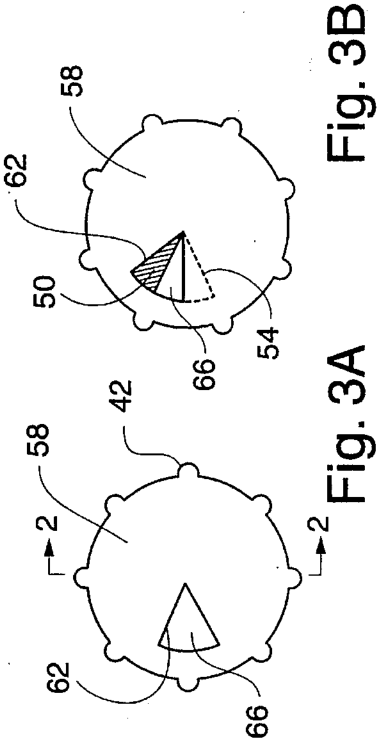
Fig. 3A
Fig. 3B
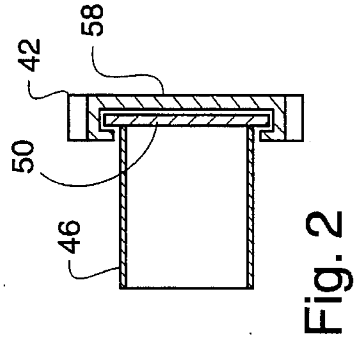
Fig. 2

PATIENT RESPIRATORY SYSTEM DRUG APPLICATOR

FIELD OF THE INVENTION

The present invention generally relates to the field of administering drugs to patients and, more particularly, to devices used to administer a typically aerosolized drug to a patient's lungs through patient inhalation.

BACKGROUND OF THE INVENTION

A variety of drugs are administered to a patient's lungs via inhalation. As in all medical-related applications, the overall cost associated with this administration of the drug is typically closely scrutinized and can affect the commercial viability of a given device. In this case, it is not so much the actual cost of the device itself, but the "costs" associated with the use of the device. That is, the "cost" of the device more specifically relates to how effective the device is in the administration of the drug to the patient's lungs. The more efficient the device is in this administration to the lungs, the less drug that is wasted which reduces the "cost" of the administration. Relatedly, the treatment time of the patient may also be reduced by a more effective drug administration to the lungs, which also reduces the "cost" of the administration.

Although there have been significant advances in devices of the noted type, optimal administration of drugs to a patient's lungs via inhalation has yet to be realized.

SUMMARY OF THE INVENTION

The present invention relates to administration of a drug to a patient's lungs through inhalation and, more particularly, to enhancing this administration such as by generating "biofeedback" to the patient regarding the patient's breathing pattern.

In one aspect, the present invention is a drug applicator which includes a drug dispenser, such as a nebulizer, and a patient inhalator, such as an inhalation mouthpiece or a mask. The drug dispenser and patient inhalator are fluidly interconnected such that the drug may be administered to the patient's lungs during inhalation. In one embodiment, the drug applicator further includes an adjustable flow regulator which regulates the air (or another appropriate oxygen-containing gas source) which the patient inhales from an appropriate source (e.g., the environment, compressed air) simultaneously with the drug. This regulation may be provided by adjusting the size of an orifice positioned between the patient inhalator and the air source through which the air flows. As such, a type of "throttling" valve may interface with a conduit which fluidly interconnects the patient inhalator and air source. The "throttling" or control valve may be utilized to provide an orifice which is adjustable between two extreme sizes and which further allows/provides for a desired degree of biofeedback regarding the patient's breathing pattern.

In another embodiment, the above-noted drug applicator may include a drug reservoir which is fluidly interconnected with the patient inhalator, as well as the drug dispenser, by a conduit. More specifically, the drug dispenser interfaces with the conduit at a location which is between the patient inhalator and the drug reservoir. That is, there is a predetermined positional relationship between these components. This predetermined positional relationship may be further defined in that the patient inhalator and drug reservoir may define opposite ends of the conduit, while the drug dispenser may interface with the sidewall of the conduit. Moreover, the conduit may further be axially extending with the patient inhalator being axially aligned therewith. Furthermore, an air source (or other appropriate oxygen-containing gas source) may be interconnected with the patient inhalator via the conduit, for instance at a location which is longitudinally displaced from the drug dispenser interface with the conduit. As such, the above-noted adjustable flow regulator may be similarly utilized in this embodiment as well.

In another embodiment, the above-noted drug applicator may include a drug reservoir, which has an inner volume ranging from about 300 milliliters to about 1,000 milliliters, and a conduit system, which fluidly interconnects the drug dispenser, patient inhalator, and drug reservoir. This conduit system includes first and second sections, with the first section fluidly interconnecting the patient inhalator with each of the drug dispenser and drug reservoir for providing the drug to the patient's lungs via inhalation, and with the second section fluidly interconnecting the patient inhalator with an air source (or other appropriate oxygen-containing gas source) for simultaneously providing air to the patient's lungs during inhalation. As such, the above-noted positional relationship between the patient inhalator, drug dispenser, and drug reservoir may be utilized. The applicator of this embodiment further includes a flow regulator which is associated with the second section of the conduit system. Consequently, the above-noted adjustable flow regulator may also be incorporated into this embodiment.

In another aspect, the present invention is a method for administering a drug to a patient's lungs and which utilizes the patient's respiratory function. Generally, the patient inhales air (or another appropriate oxygen-containing gas) from an appropriate source as well as the drug to be administered to the patient's lungs. The patient is also interconnected with a distensible drug reservoir which has a modifiable, visually observable, exterior profile. By monitoring the degree of inhalation by the patient through observation of the shape of the drug reservoir during patient inhalation and exhalation (e.g., the drug reservoir distending on exhalation and collapsing or contracting to a degree during inhalation), the drug administration process may be similarly monitored, and as such the applicator provides biofeedback to the patient and/or the patient's attendant regarding the patient's breathing pattern.

The above-noted methodology may further include a controlling of the air flow to the patient during inhalation. Increasing the air flow during patient inhalation (e.g., by increasing the size of the orifice through which the air flows to the patient) affects the patient's breathing pattern, as does decreasing this air flow (e.g., by decreasing the size of the orifice through which the air flows to the patient). This "control" may be provided by introducing a resistance to the flow of air to the patient. By increasing or decreasing this resistance, the amount of effort which the patient must exert on inhalation similarly changes, which provides adjustment capabilities to achieve the desired degree of biofeedback regarding the patient's breathing pattern.

BRIEF DESCRIPTION OF THE DRAWINGS

FIG. 1 is a perspective view of one embodiment of a patient respiratory system drug applicator;

FIG. 2 is a cross-sectional view of the control valve taken along line 2—2 in FIG. 3;

FIGS. 3A–B are front views of the extreme positions of the control valve of FIG. 1;

DETAILED DESCRIPTION

Figure 4A:
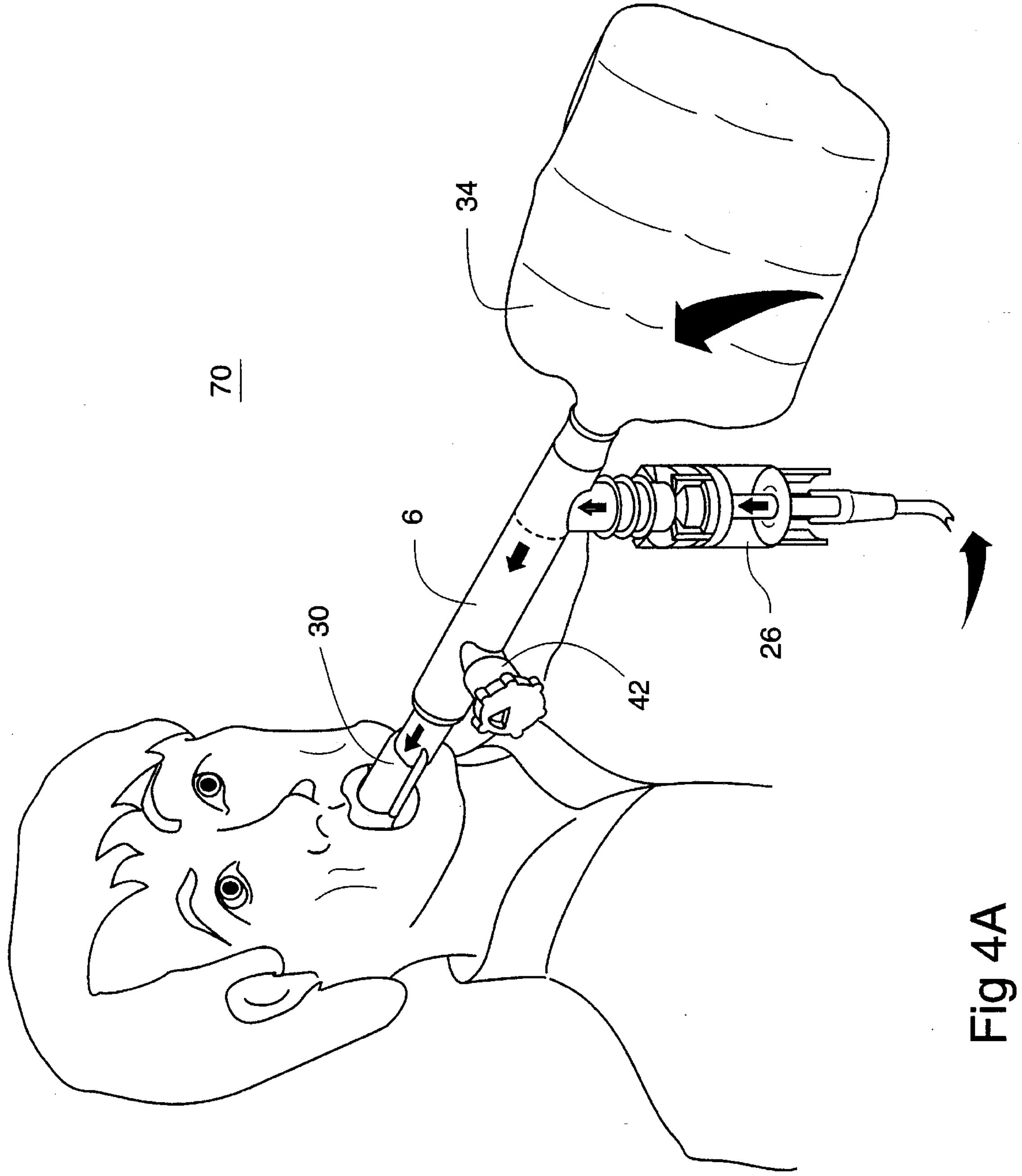
FIGS. 4A–B are views of the applicator of FIG. 1 during administration of a drug to a patient during inhalation and exhalation, respectively.

The present invention will be described with reference to the accompanying drawings which assist in illustrating its various features. A drug applicator 2 which utilizes a design for effectively administering a typically aerosolized drug to a patient's lungs via patient inhalation is illustrated in FIG. 1. Generally, the drug applicator 2 includes a patient inhalation device or inhalator 30 (e.g., a mouthpiece, breathing mask) which provides an interface between the applicator 2 and the patient. An appropriate drug dispenser 26 (e.g., a nebulizer) which provides a typically aerosolized or misted drug to the patient's lungs, through the patient inhalator 30 during inhalation by the patient, is fluidly interconnected with the patient inhalator 30. The applicator 2 further includes a control valve 42 which controls the size of an orifice through which the patient inhales air or another appropriate oxygen-containing supplemental gas simultaneously with the aerosolized drug, and which thereby effectively functions as a throttling valve. Finally, a drug reservoir 34 is incorporated into the applicator 2 which not only stores/conserves aerosolized drug which continues to be generated/provided by the drug dispenser 26 during patient exhalation (and thus while not administering drug to the patient's lungs), but which also assists in the administration of the aerosolized drug to the patient by providing biofeedback as will be discussed in more detail below (e.g., via being distensible).

The drug dispenser 26, patient inhalator 30, drug reservoir 34, and control valve 42 are fluidly interconnected, directly or indirectly, by a generally linearly or axially extending first conduit 6. The first conduit 6 includes a first port 10 which interfaces with the drug dispenser 26 and which may be a stub section integrally formed with the conduit 6, a second port 14 on one end of the first conduit 6 which interfaces with the patient inhalator 30 which in the illustrated embodiment is axially aligned with the conduit 6, a third port 18 on the opposite end of the first conduit 6 which interfaces with the drug reservoir 34, and a fourth port 22 which provides for an interface with the control valve 42 and which may be a stub section integrally formed with the conduit 6. The first port 10 and the fourth port 22 are on the sidewall of the first conduit 6, are axially displaced, and lie within planes that are generally perpendicular to each other. As such, the location at which the drug dispenser 26 interfaces with the conduit 6 is between those locations where the inhalator 30 and drug reservoir 34 interface with the conduit 6, and such is also axially displaced from the location where the control valve 42 interfaces with the conduit 6.

Drug is administered by the applicator 2 to the patient during patient inhalation. In this regard, on inhalation the patient draws in a certain amount of the air into his/her respiratory system via the fourth port 22, conduit 6, and patient inhalator 30. Moreover, aerosolized drug from the drug dispenser 26 is also drawn into the respiratory system of the patient via the first conduit 6 and patient inhalator 30, although some aerosolized drug may also flow into the drug reservoir 34 at this time. In order to enhance the administration of the aerosolized drug to the patient's lungs, the interior walls of the drug dispenser 26 may utilize a coating to minimize the formation of droplets thereon as described in U.S. Pat. No. 5,020,530 to Miller, issued, Jun. 4, 1991, the entire disclosure of which is incorporated by reference in its entirety herein. Moreover, a baffling system 28, only generally indicated in FIG. 1 but such as also described in U.S. Pat. No. 5,020,530 may be positioned between the drug dispenser 26 and the patient inhalator 30 within the first conduit 6.

The baffling system 28 contributes to a more efficient administration of the drug to the patient's lungs. It has been determined that it is desirable for the droplets of drug which are administered to the patient be within a relatively narrow size range to increase the potential for such droplets actually reaching the patient's lungs. In this regard, the baffling system 28 minimizes the potential for droplets of drug greater than a predetermined size passing through the conduit 6 to the patient inhalator 30. More specifically, the applicator 2 and including the baffling system 28 allows for the size of each of these droplets to range in size from about 0.2 microns to about 1.2 microns, and more preferably such that the mass median aerodynamic diameter (that particle size which evenly splits 50% of the aerosolized drug mass (i.e., cumulative mass) in each inhalation) is about 0.51 micrometers. As such, the applicator 2 has been able to realize lung drug depositions on the order of a minimum of 28% greater than conventional small volume nebulizers and about 900% greater than metered dose inhalers or spacers.

The baffling system 28 is multifunctional in that not only does it contribute to drug droplet size management as noted, but it also allows for only one-directional flow between the drug dispenser 26 and the inhalator 30. In this regard, the baffling system 28 prevents flow back toward the drug dispenser 26 and/or drug reservoir 34 during patient exhalation, such that the patient is forced to exhale through the fourth port 22. In order to further enhance the drug administration process, a filter (not shown) may be included in the fourth port 22 to reduce the potential for aerosolized drug being vented to the surroundings.

The drug applicator 2 includes a variety of features which further enhances the administration of the aerosolized drug to the patient's lungs. For instance, the drug applicator 2 includes the above-noted control valve 42. Generally, the control valve 42 controls the size of an orifice 66 through which air is drawn into the applicator 2 through the patient inhalator 30, and thus the "resistance" encountered by the patient during inhalation. Referring to FIGS. 2 and 3A–B, the control valve 42 interacts with the fourth port 22 which extends perpendicularly outwardly from the sidewall of the first conduit 6. The control valve 42 includes a tubular section 46 which slidably interconnects with the fourth port 22. An inner cap 50 is fixedly attached to an end of the tubular section 46 and includes an inner cap orifice 54 which defines the maximum size of the orifice 66 through the valve 42. Preferably, the maximum cross-sectional area of this orifice 54, taken perpendicularly to the flowpath therethrough (e.g., the area illustrated by the type of view presented in FIGS. 3A–B), is no greater than about 0.3 square inches (50% of the cross-sectional area of tubular section 46, having a diameter of ⅞", taken perpendicularly to the flowpath therethrough or 180° of arc), and more preferably no greater than about 0.1 square inches (16.7% of the cross-sectional area of the tubular section 46 having a diameter of about ⅞" or 60° of arc).

An outer cap 58 is disposed over the end of the inner cap 50 and is slidably rotatable relative thereto to provide for adjustability of the size of the orifice 66 through the valve 42. The outer cap 58 thereby includes an outer cap orifice 62 which is alignable at least in part with the inner cap orifice 54 and which is substantially the same size. The outer cap 58 may be moved from a first position illustrated in FIG. 3A in which the outer cap orifice 62 is completely aligned with the inner cap orifice 54 and thereby providing for a maximum size of the orifice 66 through the valve 42, to a second position illustrated in FIG. 3B in which the outer cap orifice 62 and inner cap orifice 54 are almost completely out of alignment but which nonetheless defines a minimum size of the orifice 66 through the valve 42. Preferably the cross-sectional area of the orifice 66 in FIG. 3A is not less than about 0.02 square inches (3% of the cross-sectional area of the tubular section 46 having a diameter of about ⅞" or 10° of arc).

In summary, by changing the position of the outer cap 58 relative to the inner cap 50 or more specifically the alignment of the inner cap orifice 54 relative to the outer cap orifice 62, the size of the orifice 66 through the valve 42 as a result of this alignment may be adjusted. For instance, the size of the defined orifice 66 is at a maximum in the position illustrated in FIG. 3A, while in the position illustrated in FIG. 3B the size of the defined orifice 66 is at a minimum. Although the valve 42 has been described as a control for inhaling, it of course may also be used for controlling exhaling, and thus for producing a positive expiratory pressure (PEP) which may further enhance therapy.

The drug reservoir 34 may also be used to effectively administer the aerosolized drug to the patient's lungs, namely by providing "biofeedback" to the patient and/or attendant or more specifically feedback on the patient's breathing pattern and thus the drug administration. This aspect of the applicator 2 requires that the profile of the reservoir 34 be able to change upon a change in the amount of aerosolized drug therein. For instance, the reservoir 34 may be formed from materials such as flexible vinyl sheet or later which have a degree of pliability such that upon experiencing a volume change, the profile of the reservoir 34 changes as well. However, this may not be required for other aspects of the present invention such that a substantially rigid body could be used for the applicator 2. Moreover, in one embodiment the maximum inner volume of the reservoir 34 may range from 300 milliliters to about 1,000 milliliters.

Figure 4B:
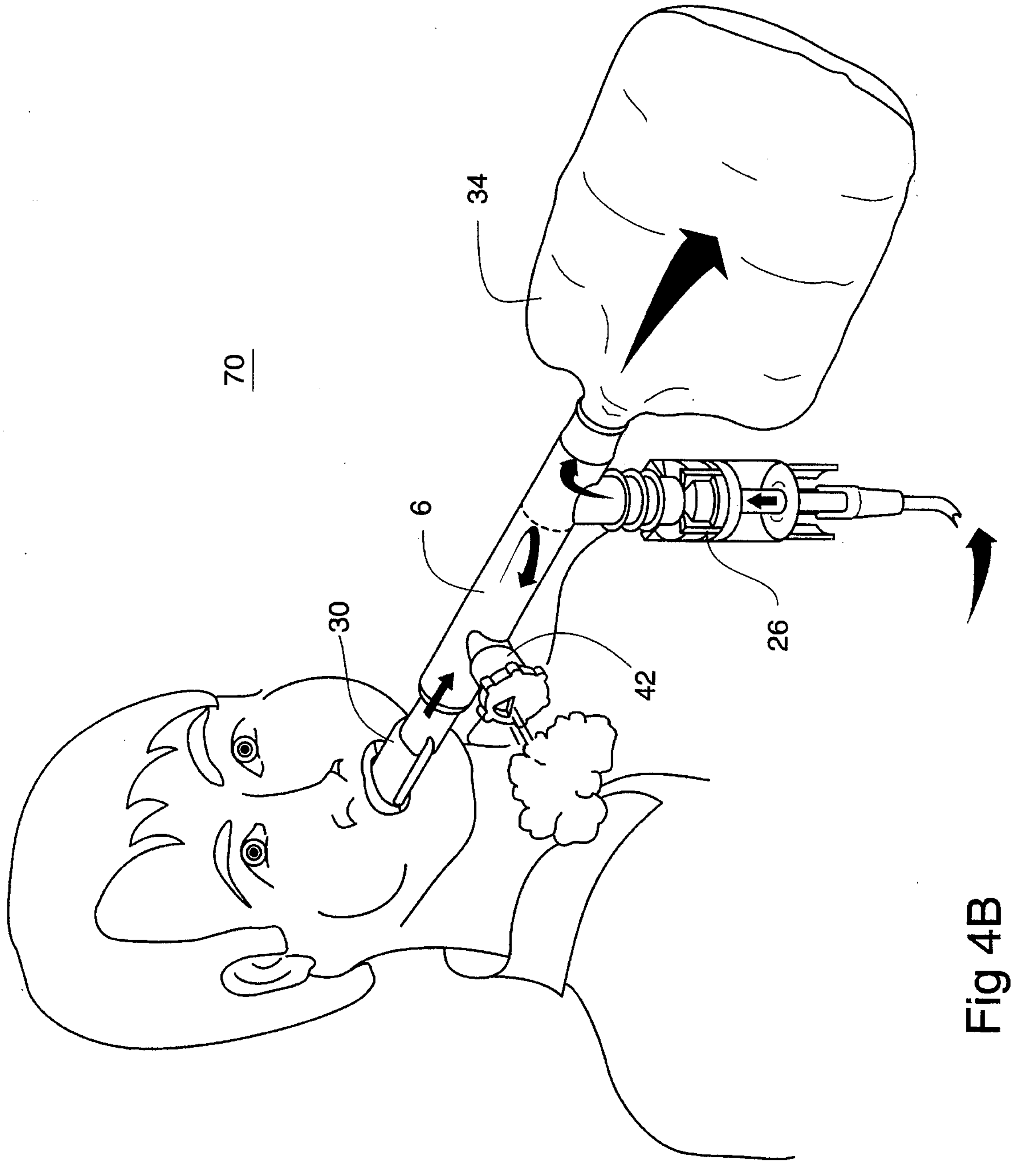

Referring to FIGS. 4A–B, one complete respiratory "cycle" of a patient is illustrated therein. As noted above, during inhalation by the patient, there is a flow of aerosolized drug from the drug dispenser 26 and/or drug reservoir 34 to the patient via the first conduit 6 and inhalator 30, as well as a flow of air from an air source (e.g., environment, compressed air) through the valve 42 and inhalator 30 to the patient's lungs. Depending upon the degree of inhalation by the patient, the drug reservoir 34 may collapse to a degree. That is, if the patient inhales more drug (aerosol volume) than is being provided by the drug dispenser 26, the drug reservoir 34 will also provide aerosolized drug to the patient. This reduction of volume of aerosolized drug within the reservoir 34 produces a visually detectable collapsing or deflation of the reservoir 34 as illustrated in FIG. 4A. When the patient exhales as illustrated in FIG. 4B, exhaustion occurs through the fourth port 22 and control valve 42. Since the baffling system 28 prevents any flow from the inhalator 30 to the reservoir 34, the reservoir 34 "expands" by receiving aerosolized drug from the drug dispenser 26 which is continuously operational during a patient's respiratory "cycle." By monitoring the degree of "pulsation" of the drug reservoir 34 (i.e., the amount of contraction/expansion on repeated inhalations and exhalations), the patient and/or medical attendant receives biofeedback on the patient's breathing pattern and thus the drug administration process.

In order to provide biofeedback to the patient and/or attendant, it may be necessary to adjust the control valve 42 in the above-noted manner. That is, in order to provide for a desired degree of "pulsation" of the drug reservoir 34, the size of the orifice 66 through the valve 42 may need to be adjusted. For instance, if there is little observable pulsation of the drug reservoir 34, the size of the orifice 66 through the control valve 42 may be reduced. Similarly, if the degree of pulsation is too great, the size of this orifice 66 may be increased.

Figure 5:
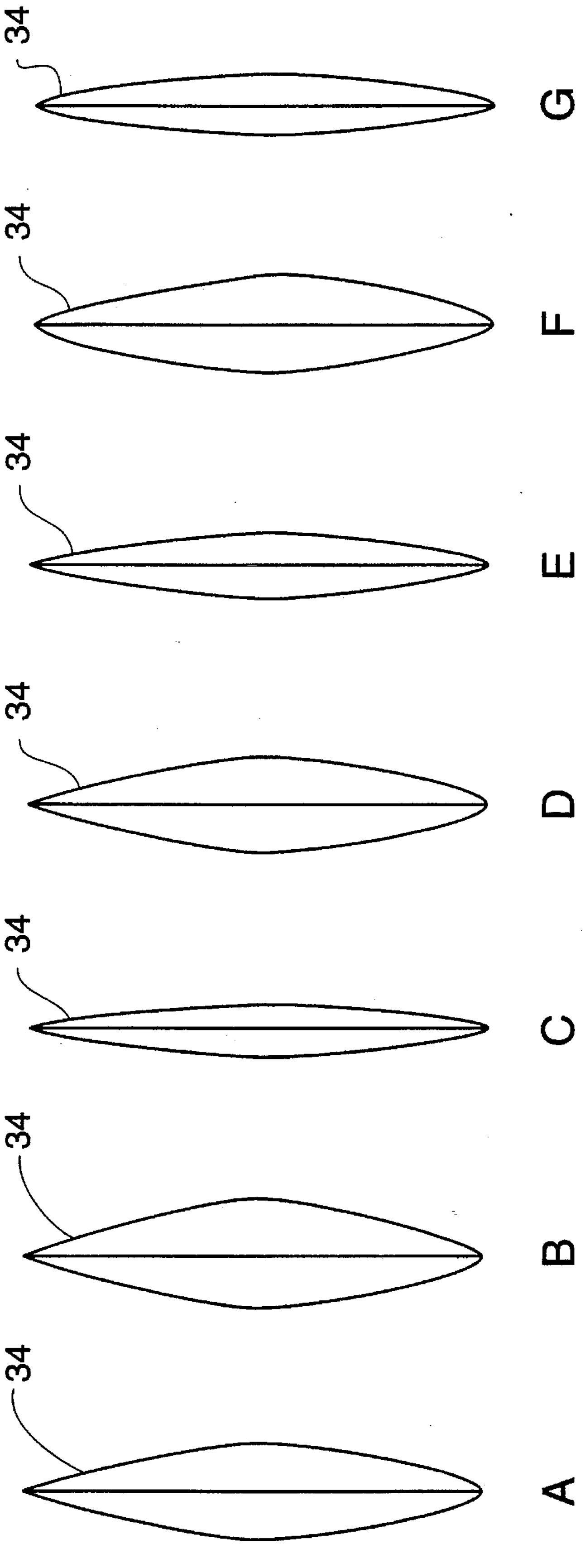
FIGS. 5A–G illustrate the distension and contraction of the distensible drug reservoir of FIG. 1 to provide biofeedback on the patient's breathing pattern.

Referring to FIGS. 5A–G, there is an illustration of the type of biofeedback provided by the applicator 2, and particularly the distensible reservoir 34. In FIGS. 5A–B, the patient is inhaling and exhaling, respectively. As can be observed by a comparison of the profiles of the distensible drug reservoir 34 in FIGS. 5A–B, there is little observable difference in its shape on a complete respiratory stroke. As such, the control valve 42 and/or the patient's subsequent breathing pattern may be adjusted such that on the subsequent inhalation by the patient illustrated in FIG. 5C, the profile of the reservoir 34 noticeably changes from that during the previous exhalation of 5C. Similarly, after the subsequent expansion of the reservoir 34 to the profile illustrated in FIG. 5D, the patient is able to "judge" the degree of inhalation such that the profile of FIG. 5C is substantially repeated in FIG. 5E, and again in FIG. 5G after an exhalation per FIG. 5F. As such, a desired breathing pattern may be achieved and closely monitored which enhances the administration of the drug to the patient.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A patient respiratory system drug applicator, comprising:

a drug dispenser;

a patient inhalator;

a first conduit fluidly interconnecting said drug dispenser and said patient inhalator and comprising first and second ports, said drug dispenser being interconnected with said first port and said second port fluidly interconnecting said patient inhalator with an oxygen source;

a distensible drug reservoir fluidly interconnected with said patient inhalator; and an adjustable flow regulator associated with said second port, wherein said adjustable flow regulator allows for an adjustment of an amount of a flow provided to the patient which is from said oxygen source and thereby also an adjustment of an amount of said flow provided to the patient which is from said distensible drug reservoir, whereby said adjustable flow regulator may be used to establish a certain pulsation of said distensible drug reservior, due to patient inhalations and exhalations, which provides biofeedback to the patient regarding the patient's breathing pattern and thereby the respiratory administration of the drug to the patient.

2. A drug applicator, as claimed in claim 1, wherein:

said drug dispenser comprises a nebulizer.

3. A drug applicator, as claimed in claim 1, wherein:

said first conduit is substantially axially extending and comprises first and second ends and a sidewall, said patient inhalator being interconnected with said first end of said first conduit in axial alignment with said first conduit, and wherein said first port is positioned on said sidewall.

4. A drug applicator, as claimed in claim 3, wherein:

said second port is on said sidewall axially displaced from and substantially perpendicular to said first port.

5. A drug applicator, as claimed in claim 4, wherein:

said distensible drug reservoir is interconnected with said second end of said first conduit.

6. A drug applicator, as claimed in claim 1, wherein:

said adjustable flow regulator comprises an orifice and a valve movable between first and second positions to change a size of said orifice, wherein a cross-sectional area of said orifice taken perpendicularly to a flowpath through said orifice with said valve in said first position is no more than about 0.3 square inches and wherein said cross-sectional area of said orifice with said valve in said second position is less than said cross-sectional area of said orifice with said valve in said first position.

7. A drug applicator, as claimed in claim 6, wherein:

said cross-sectional area of said orifice with said valve in said first position is no more than about 0.1 square inches.

8. A drug applicator, as claimed in claim 7, wherein:

said cross-sectional area of said orifice with said valve in said second position is at least about 0.02 square inches.

9. A drug applicator, as claimed in claim 1, wherein:

said patient inhalator interfaces with said first conduit on a first side of first port and wherein said drug reservoir interfaces with said first conduit on a second side of said first port.

10. A method for administering an aerosolized drug to a patient's respiratory system utilizing a distensible drug reservoir fluidly connected to the patient, comprising the steps of:

inhaling oxygen by the patient from an outside source;

providing the aerosolized drug to the patient during said inhaling step from at least the distensible drug reservior;

exhaling by the patient after said inhaling step;

monitoring a degree of said inhaling step, said monitoring step comprising preserving a changing shape of the distensible drug reservior during said inhaling and exhaling steps, wherein said observing step provides biofeedback to the patient regarding the patient's breathing pattern and thereby the respiratory administration of the aerosolized drug to the patient;

controlling an oxygen flow condition for said inhaling step, wherein said controlling step comprising providing a resistance between the outside source and the patient;

adjusting the resistance based upon said observing step, wherein said adjusting step provides an adjustment of an amount of a flow provided to the patient which is from said oxygen source and thereby also an adjustment of an amount of said flow provided to the patient which is from said distensible drug reservior, whereby said adjusting step is used to establish a certain pulsation of said distensible drug reservoir, due to patient inhalations and exhalations, which provides biofeedback to the patient regarding the patient's breathing pattern and thereby the respiratory administration of drug to the patient; and repeating said inhaling, providing, exhaling and monitoring steps a plurality of times.

11. A method, as claimed in claim 10, wherein:

said providing step comprises nebulizing the drug.

12. A method, as claimed in claim 10, wherein:

the drug reservoir has a first gas volume of the aerosolized drug in one of the inhaling steps and a second gas volume of the aerosolized drug in a subsequent exhaling step, the second volume being greater than the first volume and providing an observable difference in the shape of the drug reservoir.

13. A method, as claimed in claim 10, further comprising the step of:

changing a degree of said inhaling step based upon said observing step.

14. A method, as claimed in claim 10, further comprising the step of:

producing a greater degree of difference in the change in the shape of the distensible drug reservoir based upon said observing step.

* * * * *